US00PP08097P

United States Patent [19]

VandenBerg

[11] Patent Number: Plant 8,097

[45] Date of Patent: Jan. 12, 1993

[54] CHRYSANTHEMUM PLANT NAMED CORAL DAVIS

[75] Inventor: Cornelis P. VandenBerg, Salinas, Calif.

[73] Assignee: Yoder Brothers, Inc., Barberton, Ohio

[21] Appl. No.: 651,755

[22] Filed: Feb. 7, 1991

[51] Int. Cl.[5] ..... A01H 5/00

[52] U.S. Cl. ..... Plt./82.4

[58] Field of Search ..... Plt./74, 74.1, 82.3, Plt./82.4

[56] References Cited

U.S. PATENT DOCUMENTS

P.P. 7,325 9/1990 VandenBerg ..... Plt. 74

4,616,099 10/1986 Sparkes ..... 800/200

*Primary Examiner*—James R. Feyrer

*Attorney, Agent, or Firm*—Foley & Lardner

[57] ABSTRACT

A Chrysanthemum plant named Coral Davis particularly characterized by its flat capitulum form; daisy capitulum type; coral pink ray floret color; diameter across face of capitulum of 64 to 70 mm when fully opened, when grown as a pinched spray pot mum; photoperiodic flowering response to short days of 54 to 60 days; plant height, with 15 to 16 long days after sticking unrooted cuttings, and with 1 to 3 applications of 2500 ppm B-9 SP, ranges from 23 to 28 cm when grown as a pinched pot mum with 4 cuttings in a 15 cm pot; branching pattern is spreading, each plant having 4 to 6 laterals after pinch; and recommended as spray pot mum.

1 Drawing Sheet

The present invention comprises a new and distinct cultivar of Chrysanthemum, botanically known as *Dendranthema grandiflora*, and referred to by the cultivar name Coral Davis.

Coral Davis, identified as 4047 (84-382A03), is a product of a mutation induction program. The new cultivar was discovered and selected by Cornelis P. VandenBerg on Oct. 3, 1989 in a controlled environment in Salinas, Calif., as one flowering plant within a flowering block established as rooted cuttings from stock plants which has been exposed as unrooted cuttings to an x-ray source of 2000 rads in Fort Myers, Fla., on Mar. 30, 1989. The irradiated parent cultivar was the cultivar identified as Davis, disclosed in my U.S. Plant Pat. No. 7,325, dated Sep. 11, 1990. The parent cultivar can be generally described as a daisy spray pot mum with a flat capitulum form, a red purple ray floret color, a capitulum diameter of 64 to 70 mm when fully opened, a flowering response period of 51 to 63 days after start of short days, a plant height of 18 to 28 cm with 2 to 3 applications of 2500 ppm B-9 when grown as a pinched pot mum in a 15 cm pot, and a spreading and prolific branching pattern, with 4 to 6 laterals after pinch.

The irradiation program resulting in Coral Davis has as its primary objective the expansion of color ranges of the parent cultivar Davis. The irradiation program comprised irradiating cuttings of the parent cultivar at irradiation levels of 1500, 1750 and 2000 rads. A total of 1,466 cuttings harvested from a total of 225 irradiated plants were planted on Jul. 31, Jul. 24 and Jul. 10, 1989. Of these, 27 initial selections were made, which selections were then revegetated and reflowered. Four consecutive flowerings resulted in discarding 21 of the original 27 selections on Jul. 9, 1990. Three selections were retained and three selections were reselected as possible introductions. Reselections were made because of the fact that the flowering plants consisted of more than one color. Of these six selections, five will be commercially introduced as Coral Davis, Dark Davis, Bronze Davis, Orange Davis and Light Davis. The one remaining selection is a dark sport, and is presently being evaulated.

The first act of asexual reproduction of Coral Davis was accomplished when vegetative cuttings were taken from the initial selection in December 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Coral Davis are firmly fixed and are retained through successive generations of asexual reproduction.

Coral Davis has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Coral Davis, which, in combination, distinguish this Chrysanthemum as a new and distinct cultivar:

1. Flat capitulum form.
2. Daisy capitulum type.
3. Coral pink ray floret color.
4. Diameter across face of capitulum of 64 to 70 mm when fully opened, when grown as a pinched spray pot mum.
5. Photoperiodic flowering response to short days of 54 to 60 days.
6. Plant height, with 15 to 16 long days after sticking unrooted cuttings, and with 1 to 3 applications of 2500 ppm B-9 SP, ranges from 23 to 28 cm when grown as a pinched pot mum with 4 cuttings in a 15 cm pot.
7. Branching pattern is spreading, each plant having 4 to 6 laterals after pinch.
8. Recommended as spray pot mum.

The accompanying photographic drawing is a side view of a potted mum of Coral Davis, with four cuttings in a 15 cm pot, with the colors being as nearly true as possible with illustrations of this type.

Of the commercial cultivars known to the inventor, the most similar in comparison to Coral Davis is the parent cultivar Davis. All traits of Coral Davis are similar to those of Davis, except for the ray floret color, which is significantly darker than the ray floret color of Davis. When comparing the description of Coral Davis with Davis, it is evident that Davis has a wider range of flowering response and plant height than Coral Davis. The reason for this is that the description of Davis was based on evaluations over a two year time period, while the description of Coral Davis is based on five flowerings in a seven month period. However, in several comparative flowering trails with the parent cultivar Davis, Coral Davis has shown a one to six day slower response than Davis.

In the following description color references are made to The Royal Horticultural Society Colour Chart. The actual color of Coral Davis is not represented in the R.H.S. Colour Chart, and the values given are those believed closest to the actual color of Coral Davis. The color values were determined on plant material grown as a pinched spray pot mum in Salinas, Calif. on Dec. 4, 1990.

Classification:

*Botanical.*—*Dendranthema grandiflora* cv Coral Davis.

*Commercial.*—Flat daisy spray pot mum.

INFLORESCENCE

A. Capitulum:

*Form.*—Flat.

*Type.*—Daisy.

*Diameter across face.*—64 to 70 mm when fully opened.

B. Corolla of ray florets:

*Color (general tonality from a distance of three meters).*—Coral pink.

*Color (upper surface).*—51C to 54C, tinged with 185D.

*Color (under surface).*—179D, tinged with 185D.

*Shape.*—Straight, oblong, slightly ribbed.

C. Corolla of disc florets:

*Color (mature).*—9A.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—23 to 28 cm when grown as a pinched pot mum with 15 to 16 long days prior to start of short days, with 1 to 3 applications of 2500 ppm B-9 SP.

*Branching pattern.*—Spreading and prolific, with 4 to 6 laterals after pinch.

Foliage:

*Color (upper surface).*—147A.

*Color (under surface).*—147B.

*Shape.*—Deeply lobed and serrated.

I claim:

1. A new and distinct Chrysanthemum plant named Coral Davis, as described and illustrated.

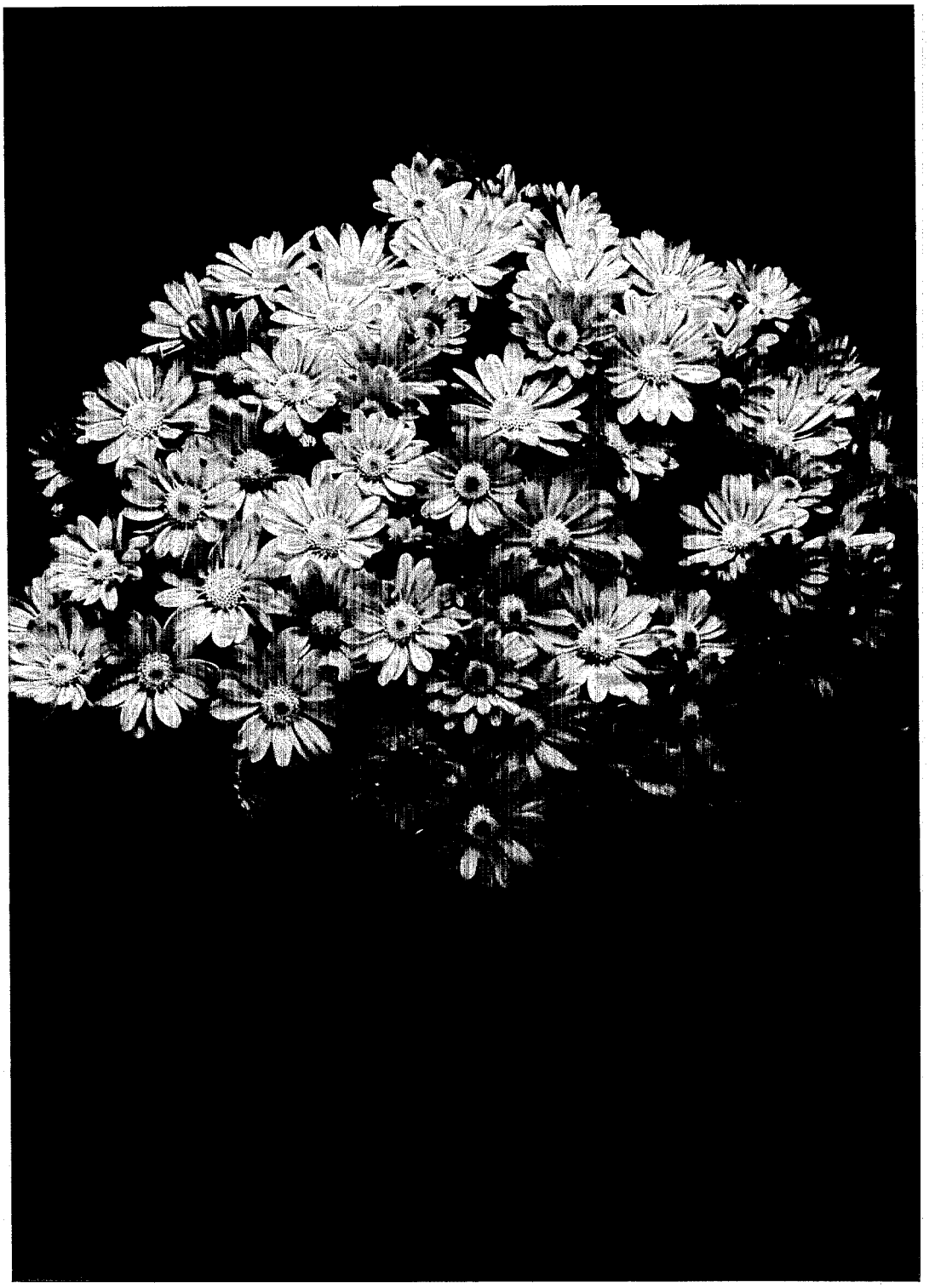

* * * * *